US006984624B2

(12) United States Patent
Dugas

(10) Patent No.: US 6,984,624 B2
(45) Date of Patent: Jan. 10, 2006

(54) COMPOSITION CONTAINING AN IRON COMPLEXING PROTEIN AND A PRECURSOR OF NITROGEN MONOXIDE METABOLISM AND/OR A CHEMICAL DONOR OF NITROGEN MONOXIDE AND USES THEREOF

(75) Inventor: Bernard Dugas, Verrieres le Buisson (FR)

(73) Assignee: Isocell S.A., Neuilly sur Seine (FR)

( * ) Notice: Subject to any disclaimer, the term of this patent is extended or adjusted under 35 U.S.C. 154(b) by 65 days.

(21) Appl. No.: 10/333,554

(22) PCT Filed: Jul. 27, 2001

(86) PCT No.: PCT/FR01/02469

§ 371 (c)(1),
(2), (4) Date: Feb. 18, 2003

(87) PCT Pub. No.: WO02/09740

PCT Pub. Date: Feb. 7, 2002

(65) Prior Publication Data

US 2004/0033945 A1    Feb. 19, 2004

(30) Foreign Application Priority Data

Jul. 27, 2000   (FR) .................................. 00 09883

(51) Int. Cl.
*A61K 38/40*    (2006.01)
*C07K 14/00*    (2006.01)

(52) U.S. Cl. ................. 514/6; 514/2; 514/12; 514/611; 530/400; 530/350; 436/69

(58) Field of Classification Search ................... 514/2, 514/12, 611, 6; 530/400, 350; 436/89; 435/325
See application file for complete search history.

(56) References Cited

U.S. PATENT DOCUMENTS 5,789,447 A      8/1998  Wink, Jr. et al.
5,827,729 A  *  10/1998  Naughton et al. ........ 435/297.2

FOREIGN PATENT DOCUMENTS

WO    WO 98/33509    8/1998

* cited by examiner

Primary Examiner—Kathleen M. Kerr
Assistant Examiner—Chih-Min Kam
(74) Attorney, Agent, or Firm—Alston & Bird LLP

(57) ABSTRACT

The invention concerns a pharmaceutical composition or a food supplement containing at least an iron complexing protein optionally in the presence of at least an iron salt, and at least a precursor of nitrogen monoxide metabolism and/or at least a chemical donor of nitrogen monoxide, the use of at least an iron complexing agent and of at least a precursor of nitrogen monoxide metabolism and/or a chemical donor of nitrogen monoxide, and optionally at least an iron salt for making pharmaceutical compositions in particular for treating asthenia or anaemia or for making a food supplement.

19 Claims, 3 Drawing Sheets

Effects of addition of an inhibitor of the L-arginine pathway on the degree of iron fixation at the cellular level

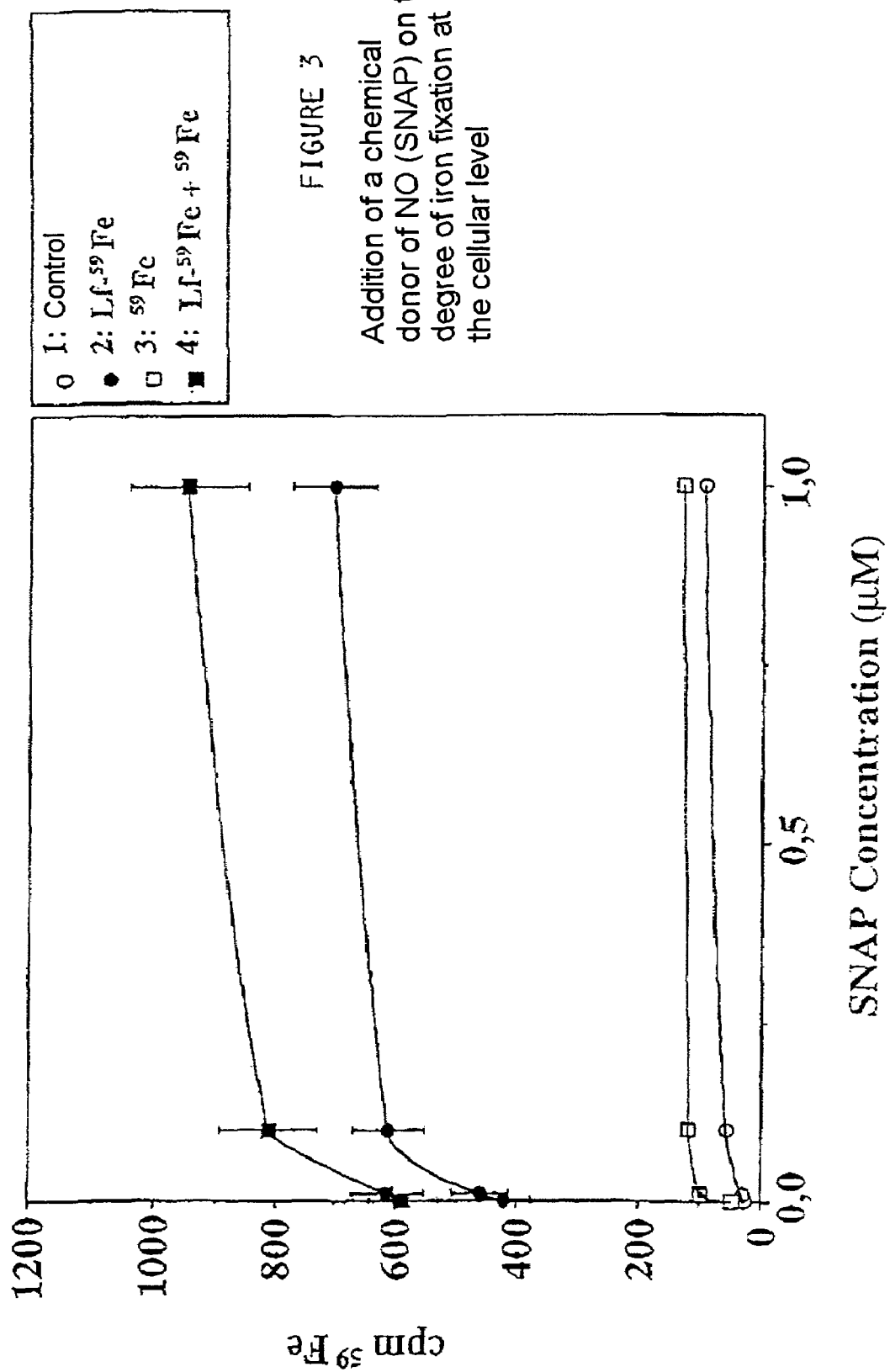

COMPOSITION CONTAINING AN IRON COMPLEXING PROTEIN AND A PRECURSOR OF NITROGEN MONOXIDE METABOLISM AND/OR A CHEMICAL DONOR OF NITROGEN MONOXIDE AND USES THEREOF

This application is a 371 of PCT/FR01/02469, filed Jul. 27, 2001, which claims the priority of French Application No. FRANCE 0009883, filed Jul. 27, 2000.

The present invention relates to a pharmaceutical composition or food supplement containing at least one iron-complexing protein and at least one precursor of nitrogen monoxide metabolism, and also to the use of at least one iron-complexing protein and of at least one precursor of NO metabolism, for producing pharmaceutical compositions intended in particular for the treatment of asthenia and/or of anemia, or for producing a food supplement.

Proteins capable of complexing iron, such as lactoferrin (Lf) and transferrin (Tf) have many biological properties.

It was thus demonstrated first of all (E. Griffiths et al., 1977, Infection & Immunity, 15 (2), 396–401) that human Lf had bactericidal activity.

Human Lf is found in most external biological secretions, such as bronchial, salivary, lacrymal, nasal, gastric, pancreatic, duodenal or vaginal secretions, and also in various biological fluids, such as synovial and amniotic fluids, and finally in plasma. Lf is found in the colostrum and the milk of most mammals. Lf concentrations in milk vary according to the species considered and the maturity of the milk. Recent studies, carried out after the cloning of bovine Lf, demonstrate that bovine Lf exhibits a 69% protein sequence identity (Pierce et al., Eur. J. Biochem., 1996, 196, 177–184).

In fact, it appears that bovine Lf has other important biological functions, other than its bactericidal activity, and that these functions are more important than those of human Lf. Specifically, it has been demonstrated that bovine Lf has immunoregulatory and antioxidant properties (Paul-Eugène et al., Compterendu de l'Académie des Sciences françaises, 1993, 316, 113–119). These observations clearly demonstrate that this type of protein, in addition to its protective activity against bacterial infections, can have a certain number of immunostimulant and antioxidant properties which are beneficial for the organism, either by regulating natural immunity or by stimulating hematopoiesis. These properties are due to the presence of receptors for Lf at the surface of several types of cell, such as enterocytes (Iyer and Lönnerdal, Eur. J. Clin. Nutr., 1993, 47, 232–241), phagocytic cells (H. S. Birgens, 1991, Danish Medical Bulletin, 38 (3), 244–252) and lymphocytes (Benneť and Davis, J. Immunol., 1981, 127, 1211–1216; Birgens et al., Br. J. Heamatol., 1983, 54, 383–388).

Lf is strongly represented in cow's milk or in the colostrum (several mg/l). Thus, its use in semipurified form in the food supplement field, and in purified form in the pharmaceutical field, can be entirely envisioned, especially to provide iron transport and fixation at the cellular level, in particular in the case of iron deficiency, to stimulate hematopoiesis in the case of anemia, to eliminate certain pathogenic bacterial agents, in particular in the digestive tract, as a functional supplement in combating food allergy and intolerance, or else as a functional supplement for certain antioxidant products, such as superoxide dismutase (SOD) for example.

Studies have demonstrated the importance of Lf in the intestinal absorption of iron. Specifically, the transport of iron into human gastrointestinal epithelial cells (Caco-2) preferentially takes place using human Lf which contains iron in complexed form, rather than using iron in free form, such as ferrous sulfate (T. M. Cox et al., 1979, Biochimica & Biophysica Acta, 558, 129–141).

Several mechanisms for making iron and Lf available have been proposed: 1) the iron is transported through the enterocyte by the supposedly intact Lf (T. Mikogami et al., 1994, American J. Physiol., 267, 308–315); 2) the iron is released at the plasma membrane (Roiron-Lagroux and Figarella, 1990, Biochimica & Biophysica Acta, 170, 837–842); 3) the iron is released after adsorption of the Lf and lysosomal degradation thereof, the degradation products being transported via the transcellular pathway (Sanchez et al., 1996, Biochimica & Biophysica Acta, 1289, 291–297).

Pharmaceutical compositions containing the combination of lactoproteins such as lactoferrin and an iron salt have also been proposed; however, this type of composition, although providing iron transport at the cellular level, does not allow fixation thereof in the cell in a long-lasting manner.

While it appears to be possible to carry out iron transport using Lf, long-lasting iron fixation at the cellular level remains a crucial factor for the use of this type of product in the treatment of anemia in particular. However, to date, no pharmaceutical composition which allows both the transport and fixation of iron at the cellular level has been proposed.

In order to remedy this problem, the inventors have developed the subject of the invention.

A subject of the present invention is therefore a pharmaceutical composition or a food supplement, characterized in that it comprises, as active principle:

at least one iron-complexing protein, optionally in the presence of at least one iron salt, and at least one precursor of nitrogen monoxide (NO) metabolism and/or at least one chemical donor of nitrogen monoxide;

and, optionally, at least one pharmaceutically acceptable vehicle.

The inventors have in fact demonstrated that long-lasting cellular iron fixation is highly potentiated in the presence of at least one precursor of NO metabolism and/or in the presence of at least one chemical donor of nitrogen monoxide.

Among the iron-complexing proteins which can be used in the pharmaceutical composition or in the food supplement in accordance with the present invention, use is preferably made of lactoferrin (Lf) or transferrin. The use of Lf is particularly preferred.

The Lf may be of bovine, equine, caprine, ovine origin, or else may be obtained synthetically or via the recombinant pathway. Among recombinant Lfs, mention may particularly be made of those which are described in the international applications WO 97/45136 and WO 98/50543.

In general, iron-complexing proteins can be used in native form, or modified form in order to increase their degree of iron saturation.

By way of example, and when Lf is used, it may thus undergo treatment at acid pH in the presence of an iron salt in order to increase its degree of iron saturation to values of greater than approximately 80%, compared to Lf in the natural state (native Lf), which exhibits a degree of iron saturation of the order of approximately 20%.

According to an advantageous embodiment of the invention, use is preferably made of a lactoferrin exhibiting a degree of iron saturation of greater than 50%, and even more preferentially of greater than 80%.

The iron-complexing protein(s) is (are) preferably used at unit doses of between approximately 0.01 mg and 5 mg, and even more preferentially between approximately 0.1 mg and 1 mg.

Among the iron salts which may optionally be used in the pharmaceutical composition or in the food supplement in accordance with the invention, mention may in particular be made of the ferrous salts (sulfate, chloride), the ferric salts (chloride, sulfate, phosphate), iron fumarate, iron oxalate, iron ascorbate, iron gluconate, iron succinate, iron acetate, and feredetate.

When they are used, the iron salt(s) may be present, in the pharmaceutical composition or in the food supplement in accordance with the invention, either in a noncomplexed form, i.e. the iron salt is not complexed with the iron-complexing protein, or in a form partially complexed or totally complexed with the iron-complexing protein.

When they are present in the pharmaceutical composition or in the food supplement in accordance with the invention, the iron salt(s) is (are) preferably used at unit doses of between approximately 0.01 and 1 mg, and even more preferentially between approximately 0.05 and 0.5 mg.

Among the precursors of NO metabolism, mention may be made of L-arginine and salts thereof such as L-arginine hydrochloride, L-arginine glutamate and L-arginine aspartate; proteins and peptides rich in L-arginine, i.e. consisting of at least 10% by weight of L-arginine, and among which mention may in particular be made of proteins and peptides derived from extracts of lupin.

Among the chemical donors of nitrogen monoxide, mention may be made of S-nitroso-N-acetylpenicillamine (SNAP).

The precursor(s) of NO metabolism and/or the chemical donor(s) of NO are preferably used at unit doses of between approximately 0.001 mg and 1 mg, and even more particularly between approximately 0.01 mg and 0.1 mg.

When L-arginine and/or a salt thereof are present in the pharmaceutical composition or in the food supplement in accordance with the invention, they are then used at unit doses of preferably between approximately 0.1 mg and 5 mg, and even more particularly between approximately 0.5 and 2 mg.

According to the invention, the iron-complexing protein(s)/precursor(s) of NO metabolism and/or chemical donor(s) of NO weight ratio is preferably between 1/1 and 10/1.

According to a particularly preferred embodiment of the invention, the iron-complexing protein(s)/precursor(s) of NO metabolism and/or chemical donor(s) of NO ratio is 1/1 (weight for weight).

According to the invention, preference is given to a pharmaceutical composition or a food supplement containing the combination of:
  from 0.01 mg to 5 mg of lactoferrin,
  from 0.01 to 1 mg of an iron salt, and
  from 0.1 mg to 5 mg of L-arginine.

According to the invention, preference is even more particularly given to a pharmaceutical composition or a food supplement containing the combination of:
  from 0.01 mg to 1 mg of lactoferrin,
  0.1 mg of an iron salt, and
  1 mg of L-arginine.

The pharmaceutical composition in accordance with the invention has the properties of being able to be used in particular for stimulating hematopoiesis in the case of anemia, and for the treatment of asthenia. In addition, by virtue of the intrinsic biological properties of lactoferrins, the pharmaceutical composition in accordance with the invention, when it contains lactoferrin as iron-complexing protein, can also be used for the elimination of pathogenic bacterial agents (in the digestive tract in particular), as a functional supplement in combating food allergy and intolerance, or else as a functional supplement in combination with certain antioxidant products, such as SOD in particular.

In this respect, a pharmaceutical composition or a food supplement in accordance with the invention, containing at least one lactoferrin as iron-complexing protein, and also SOD, is particularly preferred.

The food supplement in accordance with the invention has the property of being able to be used to prevent iron deficiencies or the risks of iron deficiency, in particular in pregnant women.

The pharmaceutical composition in accordance with the invention may also contain one or more additional active principles, such as those conventionally used in pharmaceutical compositions intended for the treatment of asthenia and/or of anemia, and among which mention may in particular be made of vitamins such as vitamin $B_{12}$, folic acid (or vitamin $B_c$) and ascorbic acid (or vitamin C); coenzyme Q10.

The pharmaceutically acceptable vehicle in accordance with the invention preferably consists of one or more excipients conventionally used for preparing pharmaceutical compositions, such as anti-aggregating agents, antioxidants, dyes, flavor modifiers, smoothing agents, assembling agents, isolating agents and, in general, any excipient conventionally used in the pharmaceutical industry.

Of course, those skilled in the art will make sure, in this instance, that the excipient(s) optionally used is (are) compatible with the intrinsic properties associated with the present invention.

The pharmaceutical composition in accordance with the invention is preferably administered orally, at a rate of one or two doses per day for 8 days.

It may be in various forms, such as in the form of tablets, capsules, drinkable suspensions, lozenges, or in any other form suitable for the oral administration method.

The food supplement in accordance with the invention is preferably absorbed orally and may be in various forms, such as in the form of tablets, capsules, drinkable suspensions, lozenges, or in any other form suitable for the usual presentation of a food supplement.

A subject of the invention is also the use of at least one iron-complexing protein and of at least one precursor of NO metabolism and/or of at least one chemical donor of nitrogen monoxide and, optionally, of at least one iron salt, for preparing a pharmaceutical composition, this composition being in particular intended for the treatment of asthenia and/or of anemia.

A subject of the invention is also the use of at least one iron-complexing protein and of at least one precursor of NO metabolism and/or of at least one chemical donor of nitrogen monoxide and, optionally, of at least one iron salt, for preparing a food supplement intended for individuals exhibiting an iron deficiency or a risk of iron deficiency, in particular pregnant women.

Besides the arrangements above, the invention also comprises other arrangements which will emerge from the following description, which refers to examples of demonstration of the potentiation of iron fixation in human gas trointestinal epithelial cells, and also to the attached figures, in which:

BRIEF DESCRIPTION OF THE DRAWINGS

FIG. 3 shows the effects of addition of a chemical donor of NO (SNAP) on the degree of iron fixation at the cellular level.

It should be clearly understood, however, that these examples are given only by way of illustration of the subject of the invention, of which they in no way constitute a limitation.

EXAMPLE 1

Demonstration of the Effect of Potentiation of Iron Fixation at the Cellular Level by a Precursor of No Metabolism The aim of this example is to demonstrate that iron fixation by Lf at the cellular level is highly potentiated in the presence of a precursor of NO metabolism, such as L-arginine.

In the natural state, bovine Lf (native bovine Lf) exhibits an iron saturation of the order of approximately 20%. Native bovine Lf was treated at pH 1 so as to substitute the unlabeled iron that it contained in the natural state with $^{59}$Fe labeled iron. Saturation of the native Lf with labeled iron resulted in a labeled lactoferrin (Lf-$^{59}$Fe) exhibiting a degree of labeled iron saturation of the order of 85% to 100%, revealed by spectrophotometric absorption at 450 nm for a specific activity of 0.03 $\mu$Ci/$\mu$g.

The Lf-$^{59}$Fe was then purified in order to remove the nonfixed labeled iron, by gel filtration on a column of SEPHADEX® G-75.

Intestinal epithelial cells of the Caco-2 line derived from a colon cancer were incubated in a proportion of $2 \times 10^6$ cells per ml in an RPMI 1640 medium buffered at pH 7.4, in the presence of 25 mmolar of Hepes, containing 15% (v/v) of fetal calf serum, 2 mmol/l of L-glutamine and 1% (v/v) of a solution of streptomycin-penicillin, sold by the company Gibco.

Iron fixation at the cellular level was then initiated by adding Lf-$^{59}$Fe and/or labeled iron and/or L-arginine.

One of the cell culture tubes received none of these three constituents, so as to act as a control.

The distribution of the constituents, and also the concentrations at which they were used, appear in Table I below:

TABLE I

| Cell culture tubes | Lf-$^{59}$Fe | Radiolabeled iron ($^{59}$Fe) | L-arginine |
| --- | --- | --- | --- |
| 1 (control) | — | — | — |
| 2 | 1 $\mu$g | — | — |
| 3 | — | — | 10 mM |
| 4 | 1 $\mu$g | — | 10 mM |
| 5 | — | 100 $\mu$g | — |
| 6 | 1 $\mu$g | 100 $\mu$g | — |
| 7 | — | 100 $\mu$g | 10 mM |
| 8 | 1 $\mu$g | 100 $\mu$g | 10 mM |

The cells were then incubated for a period of 16 hours in Eppendorf tubes kept stirring for the final 2 hours of the culture period. Throughout the incubation period, the amount of cellular iron was measured by centrifugation pellet of the cells a first time after 30 minutes (t=0.5), then after one hour (t=1), and then every hour (t=2 to t=16), using a device for measuring the radioactivity.

Figure 1:
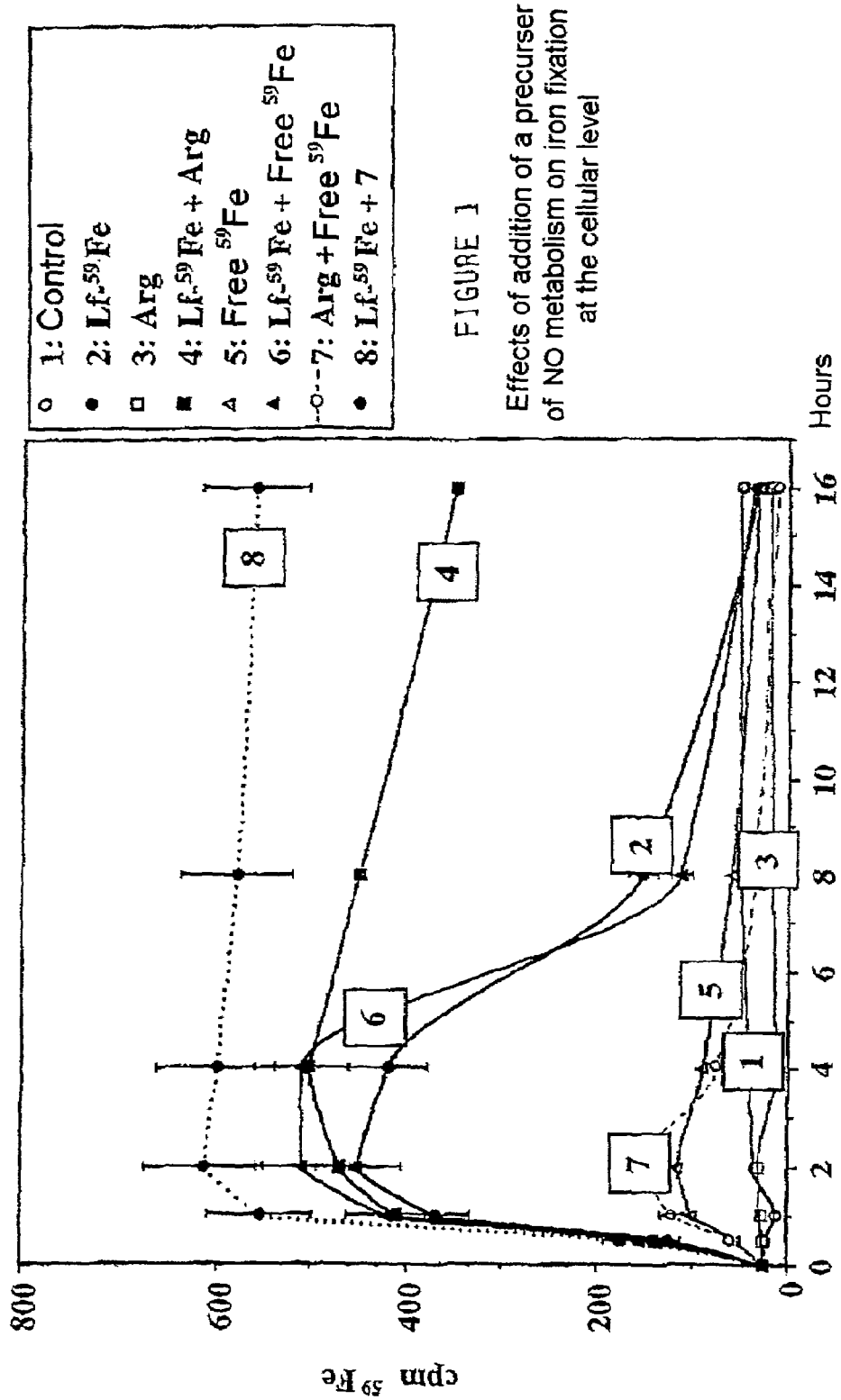
FIG. 1 shows the effects of addition of a precursor of NO metabolism on iron fixation at the cellular level.

As can be observed in FIG. 1, the iron fixation by the intestinal cells is observed from t=0.5, with a maximum between t=1 and t=2, decreasing thereafter up to t=16. This effect demonstrates that the Lf-$^{59}$Fe is capable of transporting the labeled iron into the target cell; however, this iron is only transiently fixed therein since the amount of cellular radioactive iron subsequently decreases, probably by a phenomenon of cellular leakage. When these cell cultures are supplemented with L-arginine and, optionally, with radiolabeled iron (cell cultures 4 and 8), an increase in the degree of iron fixation at the cellular level is noted, as is a prolonging of the duration of iron fixation, up to 16 hours of culture.

The addition of a precursor of NO metabolism to a pharmaceutical composition containing an iron-complexing protein and, optionally, an iron salt therefore makes it possible not only to increase the amount of iron fixed at the cellular level, but also to prolong the duration of iron fixation at the cellular level, this effect being all the more marked when said composition contains the combination of the three constituents at the same time.

Figure 2:
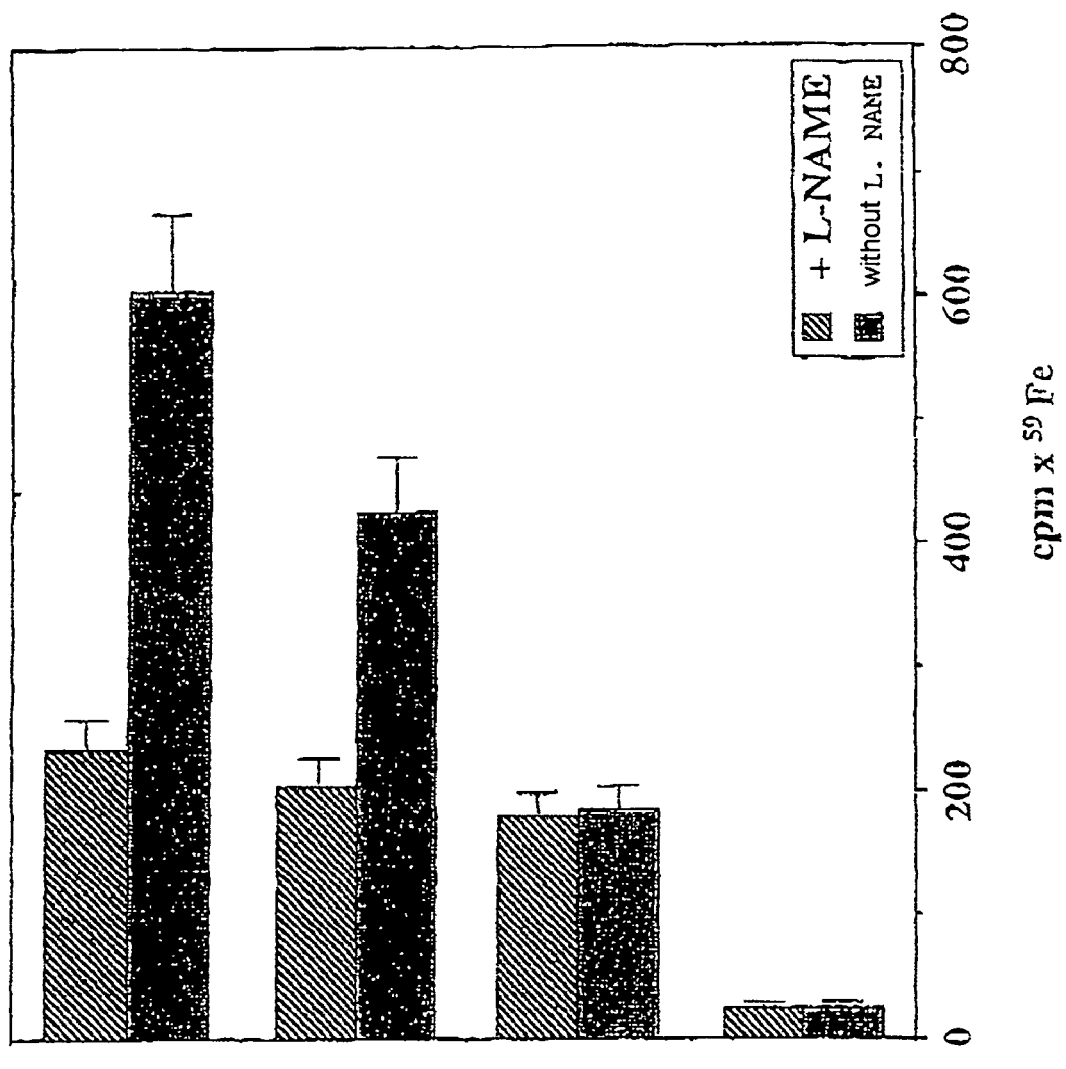
FIG. 2 shows the effects of addition of an inhibitor on the L-arginine pathway on the degree of iron fixation at the cellular level.

In addition, and as appears in FIG. 2, if the experiment carried out with the cell culture tubes 1, 2, 4 and 8 is repeated and a competitive inhibitor of the L-arginine pathway, namely N$^{\omega}$-nitro-L-arginine methyl ester (L-NAME), is added in a proportion of 1 mM to the cell culture medium of these tubes, it appears that this addition leads to a very large decrease in the degree of iron fixation at the cellular level, this being virtually returned to the degree which is observed when the cells are incubated without addition of L-arginine (tube 2). This experiment shows that, by blocking L-arginine metabolism using L-NAME, the generation of NO by the cells placed in culture is blocked, which indicates that the endogenous NO is responsible for the increase in the degree of iron fixation at the cellular level.

EXAMPLE 2

Demonstration of the Effect of Potentiation of Iron Fixation at the Cellular Level By a Chemical Donor of NO The aim of this example is to demonstrate that iron fixation by Lf at the cellular level is highly potentiated in the presence of a chemical donor of NO, such as SNAP.

Tubes of intestinal epithelial cell cultures were prepared and cultured under the same conditions as those described above in Example 1.

Iron fixation at the cellular level was then initiated by adding Lf-$^{59}$Fe and/or labeled iron.

One of the cell culture tubes received none of the constituents, so as to serve as a control.

The distribution of the constituents, and also the concentrations at which they were used, appear in Table II below:

TABLE II

| Cell culture tubes | LF-$^{59}$Fe | Radiolabeled iron ($^{59}$Fe) |
|---|---|---|
| 1 (control) | — | — |
| 2 | 1 µg | — |
| 3 | — | 100 µg |
| 4 | 1 µg | 100 µg |

The culture tubes then received SNAP in amounts ranging between 0 and 1 µM, and the cellular fixation of radiolabeled iron were then measured using a device for measuring the radioactivity.

As can be observed in FIG. 2, the addition of SNAP, to a composition containing Lf (cell culture tubes 2) and, optionally, radiolabeled iron (cell culture tubes 4) makes it possible to increase the degree of iron fixation in the epithelial cells.

Consequently, the addition of a chemical donor of NO to a pharmaceutical composition containing an iron-complexing protein and, optionally, an iron salt makes it possible to increase the degree of iron fixation at the cellular level, this effect being more marked when said composition contains the combination of the three constituents at the same time.

EXAMPLE 3

Study of the Degree of Iron Fixation at the Cellular Level as a Function of Concentrations Twelve tubes of epithelial cell cultures were prepared according to the conditions described above in Example 1.

Iron fixation at the cellular level was then initiated by adding Lf-$^{59}$Fe and/or labeled iron and/or L-arginine.

One of the cell culture tubes received none of these three constituents, so as to act as a control.

The distribution of the constituents, and also the concentrations at which they were used, appear in Table III below:

| Cell culture tubes | Lf-$^{59}$Fe in mg/ml | Radiolabeled iron ($^{59}$Fe) in mg/ml | L-arginine in mg/ml |
|---|---|---|---|
| Control | — | — | — |
| 1 | 1 | — | — |
| 2 | 0.1 | — | — |
| 3 | 0.01 | — | — |
| 4 | — | 0.1 | — |
| 5 | 1 | 0.1 | — |
| 6 | 0.1 | 0.1 | — |
| 7 | 0.01 | 0.1 | — |
| 8 | — | — | 1 |
| 9 | 1 | 0.1 | 1 |
| 10 | 0.1 | 0.1 | 1 |
| 11 | 0.01 | 0.1 | 1 |

The degree of cellular fixation of iron was measured after 72 hours of incubation using a device for measuring the radioactivity.

The results obtained for each of the 12 tubes appear in Table IV below:

TABLE IV

| Cell culture tubes | Degree of iron fixation in the cells (cpm $^{59}$Fe) |
|---|---|
| Control | 1 |
| 1 | 1.2 ± 0.1 |
| 2 | 1.0 ± 0.2 |
| 3 | 1.1 ± 0.1 |
| 4 | 1.8 ± 0.1 |
| 5 | 2.1 ± 0.2 |
| 6 | 1.9 ± 0.1 |
| 7 | 1.7 ± 0.1 |
| 8 | 1 |
| 9 | 5.4 ± 0.3 |
| 10 | 4.3 ± 0.2 |
| 11 | 3.1 ± 0.1 |

These results show that, at the three concentrations of Lf tested, a very large increase in the degree of iron fixation at the cellular level is observed when the cell culture medium contains at the same time an iron-complexing protein, an iron salt and a precursor of NO metabolism, thus proving the essential role that L-arginine plays in the potentiation of iron fixation by cells.

What is claimed is:

1. A pharmaceutical composition or a food supplement, characterized in that it consists essentially of, as active principle:
   (i) lactoferrin as an iron-complexing protein,
   (ii) at least one iron salt,
   (iii) at least one
      a) precursor of nitrogen monoxide metabolism selected from the group consisting of L-arginine and salts thereof;
      b) S-nitrso-N-acetyl-penicillamine as a chemical donor of nitrogen monoxide; and/or
      c) a mixture thereof; and
   (iv) a pharmaceutically acceptable vehicle.

2. The pharmaceutical composition or food supplement as claimed in claim 1, wherein said lactoferrin is from bovine, equine, caprine, or ovine origin, or is obtained synthetically or recombinantly.

3. The pharmaceutical composition or food supplement as claimed in claim 2, wherein said lactoferrin exhibits a degree of iron saturation of greater than 50%.

4. The pharmaceutical composition or food supplement as claimed in claim 1, wherein said iron-complexing protein is used at unit doses of between 0.01 mg and 5 mg.

5. The pharmaceutical composition or food supplement as claimed in claim 4, wherein said iron-complexing protein is used at unit doses of between 0.1 mg and 1 mg.

6. The pharmaceutical composition or food supplement as claimed in claim 1, wherein said iron salt is selected from the group consisting of ferrous salts, ferric salts, iron fumarate, iron oxalate, iron ascorbate, iron gluconate, iron succinate, iron acetate, and feredetate.

7. The pharmaceutical composition or food supplement as claimed in claim 1, wherein said iron salt is present in said composition or said food supplement in the form of a mixture of noncomplexed iron and iron totally complexed with said iron-complexing protein, or in a totally complexed form with said iron-complexing protein.

8. The pharmaceutical composition or food supplement as claimed in claim 7, wherein said iron salt is used at unit doses of between 0.01 and 1 mg.

9. The pharmaceutical composition or food supplement as claimed in claim 8, wherein said iron salt is used at unit doses of between 0.05 and 0.5 mg.

10. The pharmaceutical composition or food supplement as claimed in claim 1, wherein said precursor of nitrogen monoxide metabolism is a L-arginine salt selected from the group consisting of L-arginine hydrochloride, L-arginine glutamate and L-arginine aspartate.

11. The pharmaceutical composition or food supplement as claimed in claim 1, wherein said precursor of nitrogen monoxide metabolism anti the chemical donor of nitrogen monoxide are used at unit doses of between 0.001 mg and 1 mg.

12. The pharmaceutical composition or food supplement as claimed in claim 11, wherein said precursor of nitrogen monoxide metabolism and the chemical donor of nitrogen monoxide are used at unit doses of between 0.01 mg and 0.1 mg.

13. The pharmaceutical composition or food supplement as claimed in claim 1, wherein said iron-complexing protein/ precursor of nitrogen monoxide metabolism and/or said iron-complexing protein/chemical donor of nitrogen monoxide weight ratio is between 1/1 and 10/1.

14. The pharmaceutical composition or food supplement as claimed in claim 13, wherein said iron-complexing protein/precursor of nitrogen monoxide metabolism and/or said iron-complexing protein/chemical donor of nitrogen monoxide weight ratio is 1/1.

15. The pharmaceutical composition or food supplement as claimed in claim 1, containing the combination of:
  (a) from 0.01 mg to 5 mg of lactoferrin;
  (b) from 0.01 to 1 mg of an iron salt; and
  (c) from 0.1 mg to 5 mg of L-arginine.

16. The pharmaceutical composition or food supplement as claimed in claim 15, containing the combination of:
  (a) from 0.01 mg to 1 mg of lactoferrin
  (b) 0.1 mg of an iron salt; and
  (c) 1 mg of L-arginine.

17. The pharmaceutical composition or food supplement as claimed in claim 1, further comprising superoxide dismutase.

18. A method for preparing a pharmaceutical composition for the treatment of asthenia or anemia which comprises incorporating into the composition:
  (i) lactoferrin as an iron-complexing protein,
  (ii) at least one
    a) precursor of nitrogen monoxide metabolism selected from the group consisting of L-arginine and salts thereof;
    b) S-nitrso-N-acetyl-penicillamine as a chemical donor of nitrogen monoxide; and/or
    c) a mixture thereof; and
  (iii) at least one iron salt.

19. A method for preparing a food supplement which comprises incorporating into the food supplement:
  (i) lactoferrin as an iron-complexing protein,
  (ii) at least one
    a) precursor of nitrogen monoxide metabolism selected from the group consisting of L-arginine and salts thereof;
    b) S-nitrso-N-acetyl-penicillamine as a chemical donor of nitrogen monoxide; and/or
    c) a mixture thereof; and
  (iii) at least one iron salt.

* * * * *